US011925576B2

(12) United States Patent
Stark et al.

(10) Patent No.: US 11,925,576 B2
(45) Date of Patent: Mar. 12, 2024

(54) WARMING SYSTEM WITH SENSOR

(71) Applicant: 3M INNOVATIVE PROPERTIES COMPANY, St. Paul, MN (US)

(72) Inventors: John R. Stark, Saint Paul, MN (US); Jared J. Balthazor, Linwood Township, MN (US); Philip G. Dion, Blaine, MN (US); Jay R. Goetz, Deephaven, MN (US); Leroy J. Longworth, Woodbury, MN (US); Melissa T. Nelson, Woodbury, MN (US); Tyler J. Sandback, Prior Lake, MN (US); Michele A Waldner, Hudson, WI (US); Michael J. Woodson, West Saint Paul, MN (US)

(73) Assignee: 3M INNOVATIVE PROPERTIES COMPANY, St. Paul, MN (US)

(*) Notice: Subject to any disclaimer, the term of this patent is extended or adjusted under 35 U.S.C. 154(b) by 344 days.

(21) Appl. No.: 17/305,394

(22) Filed: Jul. 7, 2021

(65) Prior Publication Data

US 2022/0015940 A1   Jan. 20, 2022

Related U.S. Application Data

(60) Provisional application No. 63/052,359, filed on Jul. 15, 2020.

(51) Int. Cl.
*A61F 7/00* (2006.01)
*G01K 3/08* (2006.01)
*G01K 13/024* (2021.01)
*G01L 19/00* (2006.01)

(52) U.S. Cl.
CPC .............. *A61F 7/0085* (2013.01); *G01K 3/08* (2013.01); *G01K 13/024* (2021.01); *G01L 19/0092* (2013.01); *A61F 2007/006* (2013.01); *A61F 2007/0086* (2013.01); *A61F 2007/0096* (2013.01)

(58) Field of Classification Search
CPC ........ A61F 2007/0059; A61F 2007/006; A61F 2007/0086; A61F 2007/0096; A61F 7/0085; A61F 7/0097; G01K 13/024; G01K 3/08; G01K 3/14; G01L 19/0092
See application file for complete search history.

(56) References Cited

U.S. PATENT DOCUMENTS 6,126,681 A * 10/2000 Van Duren ........... A61F 7/0097
                                                           601/16
2004/0204748 A1 * 10/2004 Hansen ................. A61F 7/0085
                                                           607/104

* cited by examiner

*Primary Examiner* — Tigist S Demie
(74) *Attorney, Agent, or Firm* — Jeffrey M. Olofson (57) ABSTRACT

An air hose includes a corrugated flexible hose. The air hose also includes a first hose end section mechanically coupled to the corrugated flexible hose. The first hose end section includes a pressure sensor communicatively coupled to a warming unit. The first hose end section is configured to releasably couple to a pneumatic convective device. The air hose also includes a second hose end section mechanically coupled to the corrugated flexible hose. The second hose end section is configured to couple to the warming unit.

15 Claims, 10 Drawing Sheets

WARMING SYSTEM WITH SENSOR

TECHNICAL FIELD

The present disclosure relates to a warming system having a warming unit and an air hose. More particularly, the present disclosure relates to the warming system including one or sensors.

BACKGROUND

A warming device, and more particularly, a forced-air warming device can be used in a medical setting to deliver a stream of pressurized, warm air to a patient for maintaining a body temperature of the patient. The warming device typically includes a warming unit and an air hose connected to the warming unit. An operation of the warming unit can be controlled in order to vary characteristics of the pressurized, warm air being directed towards the patient. The pressurized, warm air is generally distributed over a wider area to reduce a probability of direct impingement of the pressurized, warm air on the patient. However, in practices such as free hosing, the pressurized, warm air may directly impinge on the patient and may cause thermal injuries to the patient, which is not desirable.

Moreover, factors such as reduction in a flow rate of the pressurized, warm air delivered by the warming device may cause less than desired heat to be transferred to the patient which may not be sufficient to provide thermal comfort. Such reduction in the flow rate can be a result of blockages in the warming device and/or use of incompatible blankets. Thus, it may be desirable to detect practices or conditions that interfere with an effectiveness of the warming device and accordingly generate alerts or alter a therapy being provided by the warming device.

BRIEF SUMMARY

In a first aspect of the present disclosure, an air hose is provided. The air hose includes a corrugated flexible hose. The air hose also includes a first hose end section mechanically coupled to the corrugated flexible hose. The first hose end section includes a pressure sensor communicatively coupled to a warming unit. The first hose end section is configured to releasably couple to a pneumatic convective device. The air hose also includes a second hose end section mechanically coupled to the corrugated flexible hose. The second hose end section is configured to couple to the warming unit.

In a second aspect of the present disclosure, a system is provided. The system includes the air hose of the first aspect. The system also includes a warming unit that can provide a stream of pressurized, heated air. The warming unit includes a heater control circuitry. The warming unit also includes a power conversion apparatus for converting Alternating Current (AC) power for use by the heater control circuitry.

BRIEF DESCRIPTION OF THE SEVERAL VIEWS OF THE DRAWINGS

To easily identify the discussion of any particular element or act, the most significant digit or digits in a reference number refer to the figure number in which that element is first introduced.

DETAILED DESCRIPTION

In the following description, reference is made to the accompanying figures that form a part thereof and in which various embodiments are shown by way of illustration. It is to be understood that other embodiments are contemplated and may be made without departing from the scope or spirit of the present disclosure. The following detailed description, therefore, is not to be taken in a limiting sense.

In the context of present disclosure, the terms "first" and "second" are used as identifiers. Therefore, such terms should not be construed as limiting of this disclosure. The terms "first" and "second" when used in conjunction with a feature or an element can be interchanged throughout the embodiments of this disclosure.

The present disclosure generally relates to warming devices, and more specifically, forced-air warming devices that include a warming unit and an air hose coupled to the warming unit. The teachings of this disclosure are directed towards detection of one or more operating characteristics that interfere with usage of the warming devices using sensors, such as pressure sensors and temperature sensors.

Further, the one or more pressure sensors may be positioned within a static pressure region defined by the first hose end section. The static pressure region is configured to isolate static pressure from an airflow path. In one example, the static pressure region does not experience significant variations in pressure readings (e.g., no greater than +/−25% variation in pressure readings while the warming unit is activated). In some examples, the static pressure region is defined proximate or adjacent to an inside surface of the first hose end section. Accordingly, the pressure sensors may be positioned proximate the inside surface (within the static pressure region). For example, the pressure sensor can be placed along the wall of the first hose end section. Positioning the pressure sensors in the static pressure region may provide stabilized pressure readings and may eliminate dynamic pressure caused by an airflow. In another example, the static pressure region includes a cavity such that the one or more pressure sensors is positioned within the cavity. The cavity is offset from the airflow path. As the pressure sensors are mounted off the airflow path, the pressure sensors may provide stabilized pressure readings.

Further, in some examples, alerts may be generated based on the detection of unusual operating characteristics in order to notify a user, such as a medical personnel, regarding a current condition of the warming device. Such alerts may pertain to misuse of the warming device, blockages in the air hose or the warming unit, usage of incompatible devices, and the like. In other examples, one or more parameters of the warming unit may be automatically adjusted based on the detection of the unusual operating characteristics that interfere with usage of the warming devices.

Figure 1:
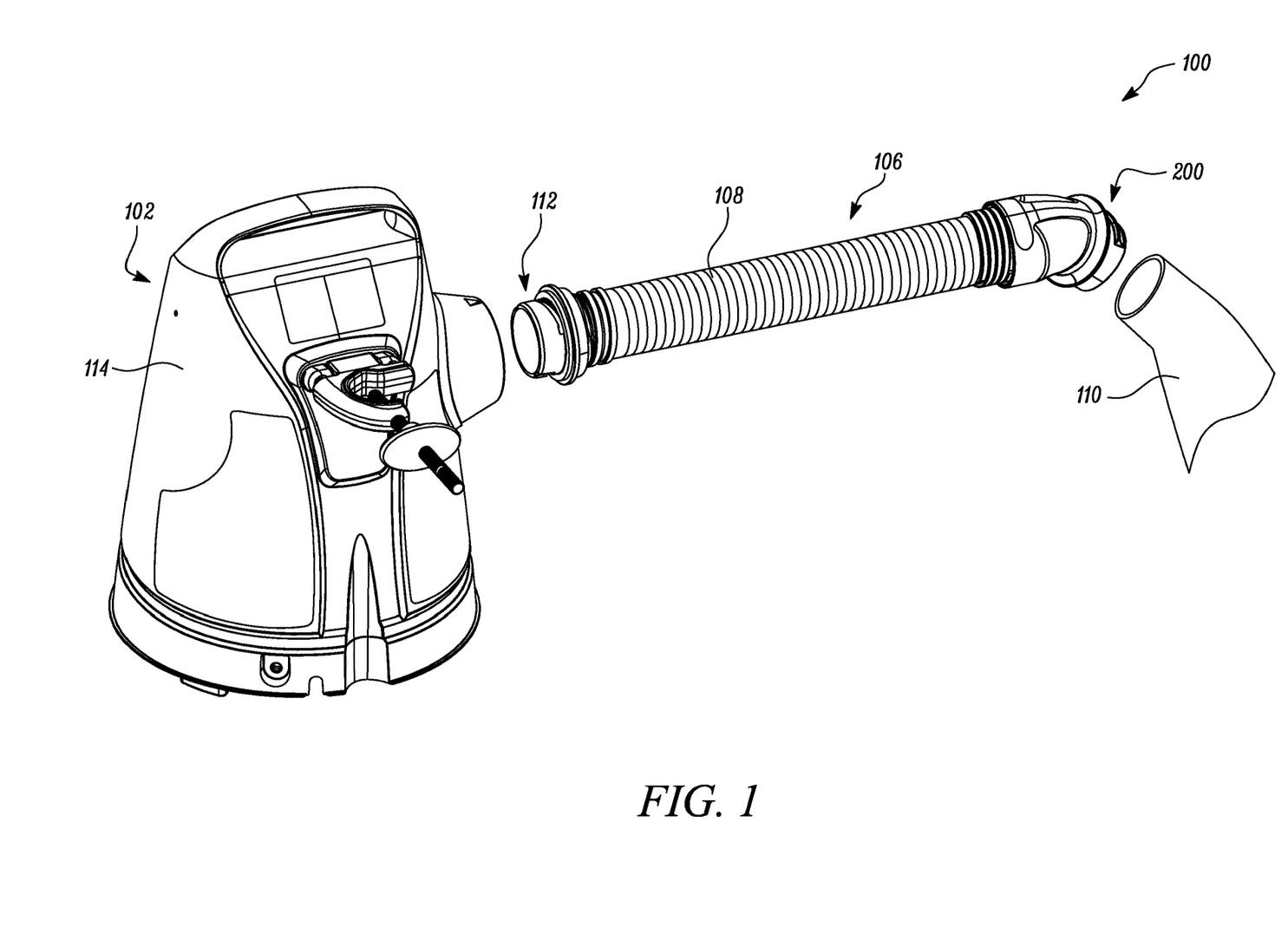
FIG. 1 illustrates a warming system, in accordance with one embodiment.

Referring to FIG. 1, an exemplary warming system 100 is illustrated. The warming system 100 may be hereinafter interchangeably referred to as the system 100. The warming system 100 includes a warming unit 102 that can provide a stream of pressurized, heated air. Details pertaining to the warming unit 102 will be explained later in this section in relation to FIG. 4. Further, the warming system 100 also includes an air hose 106. The air hose 106 includes a corrugated flexible hose 108. The corrugated flexible hose 108 can be manufactured of a plastic material, a rubber material, silicone, and the like. The air hose 106 includes a first hose end section 200 mechanically coupled to the corrugated flexible hose 108. The first hose end section 200 has a cross-section 201 formed from an ellipsoid (see FIG. 3A). The first hose end section 200 can be generally elbow shaped. In an example, the first hose end section 200 can be coupled to the corrugated flexible hose 108 using helical threads. In another example, the first hose end section 200 can be press fitted to the corrugated flexible hose 108. In yet another example, other techniques such as adhesives or overmolding may be used to couple the first hose end section 200 to the corrugated flexible hose 108, without limiting the scope of the present disclosure. The first hose end section 200 can be made of a plastic material.

The first hose end section 200 is configured to releasably couple to a pneumatic convective device 110. A portion of the pneumatic convective device 110 is illustrated herein. The pneumatic convective device 110 is embodied as an inflatable device that inflates based on receipt of pressurized, heated air. Further, the pneumatic convective device 110 distributes the pressurized, heated air being directed towards a patient. In an example, the pneumatic convective device 110 may embody a thermal blanket or a garment, as per application requirements. The pneumatic convective device 110 is fluidically coupled to the first hose end section 200. Thus, the first hose end section 200 provides fluid communication between the corrugated flexible hose 108 and the pneumatic convective device 110. The pneumatic convective device 110 can include a port (not shown) that is coupled with the first hose end section 200. In various examples, the pneumatic convective device 110 can be coupled to the first hose end section 200 by a press fit, snap fit, or the pneumatic convective device 110 can be coupled to the first hose end section 200 using helical threads, adhesives, or overmolding. Further, any other coupling technique may be used to couple the pneumatic convective device 110 to the first hose end section 200.

Figure 2:
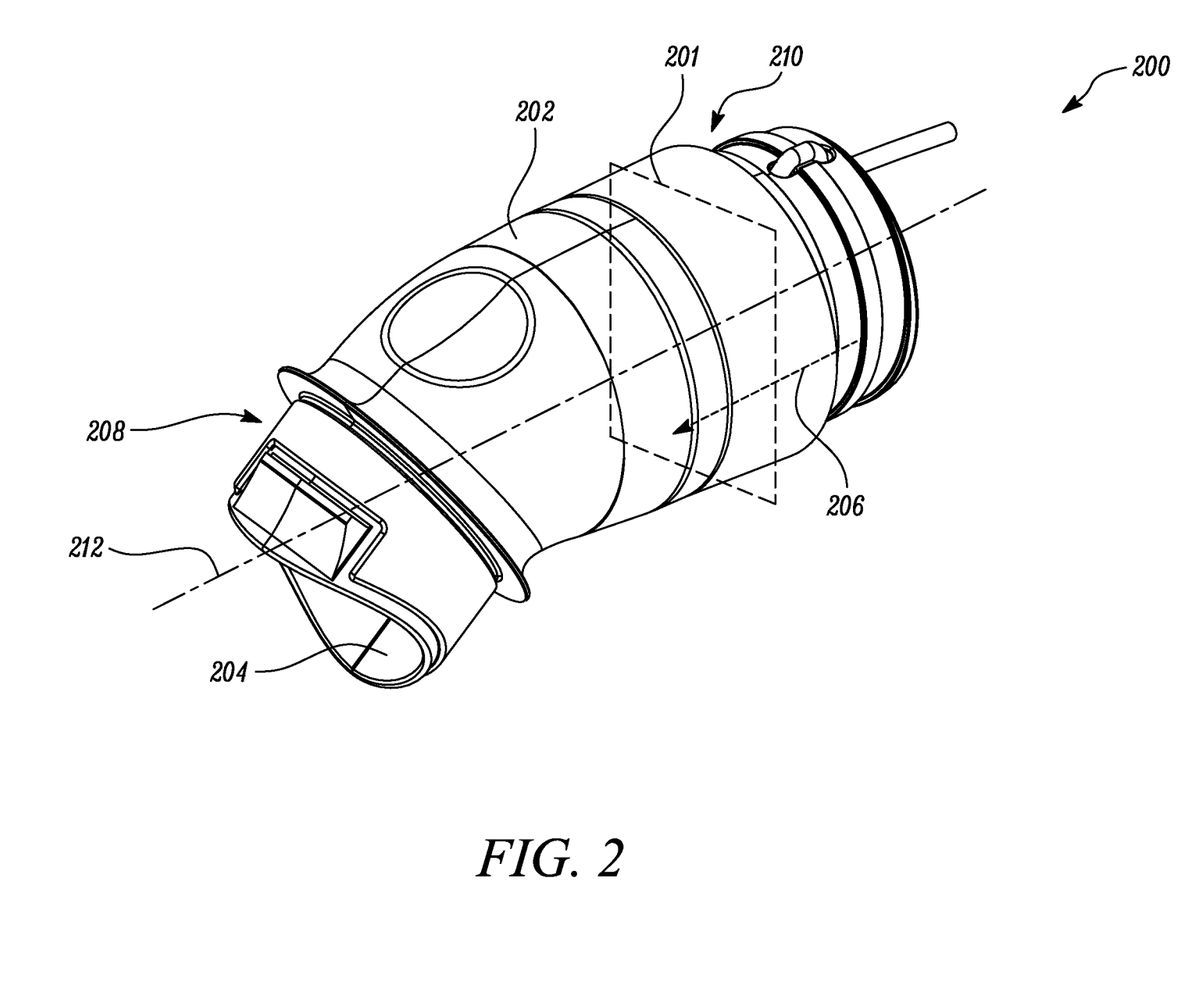
FIG. 2 illustrates a perspective view of a first hose end section associated with the warming system of FIG. 1, in accordance with one embodiment.

As shown in FIG. 2, the first hose end section 200 has an outside surface 202 facing an environment and an inside surface 204 facing an airflow path 206. The airflow path 206 may be defined as a path followed by the pressurized, heated air being directed towards the pneumatic convective device 110 (see FIG. 1) from the warming unit 102 (see FIG. 1). Further, the inside surface 204 surrounds at least a portion of the airflow path 206. The first hose end section 200 can be a single, integrated part or can include multiple parts. For example, the first hose end section 200 is shown including a first end part 208 and a second end part 210. The first end part 208 and the second end part 210 are attached such that the first end part 208 is rotatable about a longitudinal axis 212 relative to the second end part 210. In some examples, the first end part 208 can be coupled with the second end part 210 by a friction fit.

Further, the first hose end section 200 comprises a static pressure region 215 adjacent to the inside surface 204. The static pressure region 215 is a region of the first hose end section 200 that isolates static pressure from the airflow path 206. In some examples, the term "static pressure region" as used herein may be defined as a region that may eliminate dynamic pressure caused by an airflow 254 (shown in FIG. 4) and provide stabilized pressure readings. Further, the static pressure region 215 can include a cavity 218. It should be noted that a position of the static pressure region 215 and the cavity 218 illustrated herein is exemplary in nature.

Figure 3A:
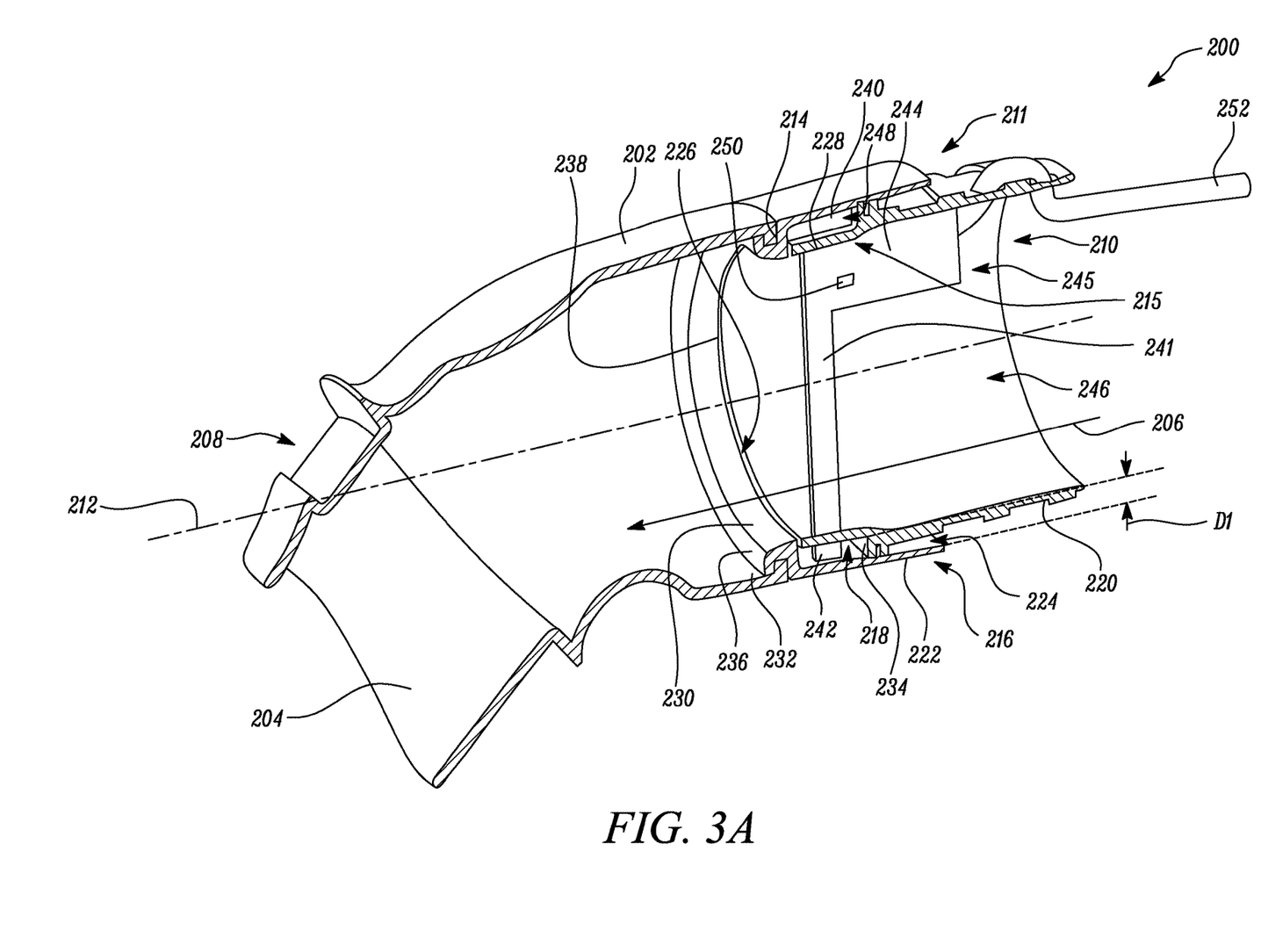
FIG. 3A illustrates a cross-sectional view of the first hose end section of FIG. 2, in accordance with one embodiment.
Figure 3B:
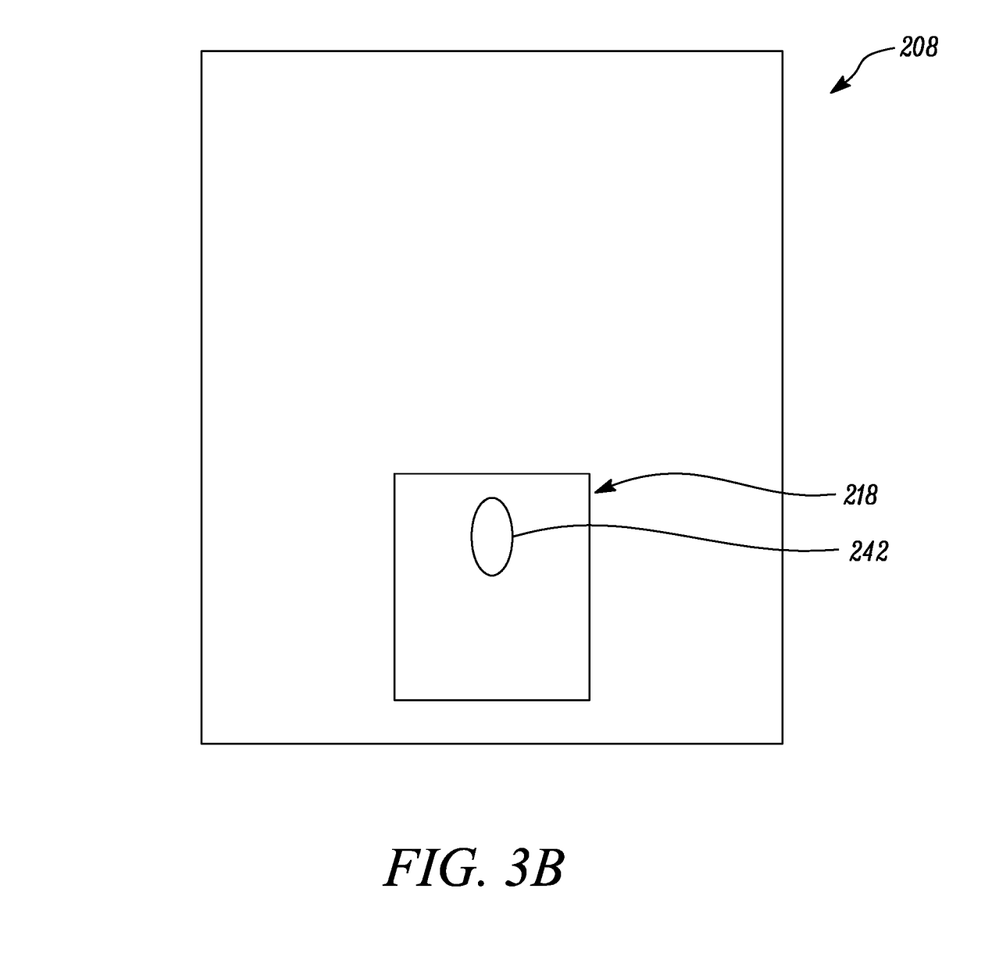
FIG. 3B illustrates a schematic view of the first hose end section of FIG. 2, in accordance with another embodiment.

With respect to FIGS. 3A-3B, the cavity 218 can be fluidically coupled to the airflow path 206 formed by the first hose end section 200. As discussed herein, the cavity 218 can be formed exclusively within a wall of the first end part 208, the second end part 210, or formed between the combination of both the first end part 208 and the second end part 210. A pressure sensor 240 can be disposed within the cavity 218. Referring to FIG. 3A, the first end part 208 comprises a lip 214 proximate an end 216 of the first end part 208. The first end part 208 is configured to releasably attach to the pneumatic convective device 110 (see FIGS. 1 and 4). Moreover, the second end part 210 is configured to attach to the corrugated flexible hose 108 (see FIG. 1) at one end 211 such that a pneumatic seal is formed between the corrugated flexible hose 108 and the second end part 210. The second end part 210 can include an outer wall 222 and/or an inner wall 220.

The cavity 218 is disposed such that the airflow path 206 is longitudinal with the corrugated flexible hose 108 and the first hose end section 200 and the cavity 218 is offset from the airflow path 206. In one example, the cavity 218 is radially offset from the airflow path 206. Moreover, the cavity 218 is fluidically coupled to the airflow path 206 via the inside surface 204 but not the outside surface 202 of the first hose end section 200. The cavity 218 is formed around at least half of an inner perimeter 236 of the first hose end section 200 (e.g., as defined by the inner wall 220 or the outer wall 222). In other examples, the cavity 218 may be formed around the inner perimeter 236 of the first hose end section 200. The cavity 218 forms an annulus 238 that allows air from the airflow path 206 to enter.

In one embodiment, the second end part 210 includes the cavity 218. More particularly, the second end part 210 includes the inner wall 220 and the outer wall 222, such that a space 224 defined between the inner wall 220 and the outer wall 222 forms the cavity 218. A distance "D1" between the inner wall 220 and the outer wall 222 can be between 30 and 40 thousandths of an inch. Further, the distance "D1" between the inner wall 220 and the outer wall 222 may vary as per application requirements. The inner wall 220 and the outer wall 222 form a first opening 226 between an end 228 of the inner wall 220 and a recessed portion 230 of the outer wall 222 that allows air from the airflow path 206 to enter. More particularly, the outer wall 222 of the second end part 210 includes the recessed portion 230 configured to mate with the lip 214 such that the second end part 210 is rotatable relative to the first end part 208.

In another embodiment, as illustrated in FIG. 3B, the cavity 218 may be formed in the first end part 208. As shown in FIG. 3A, it should be noted that the cavity 218 may be defined by any one or both of the first and second end parts 208, 210 provided the cavity 218 is off set from the airflow path 206. Similarly, the cavity 218 can be formed by an inner wall of the first hose end section 200 and an outer wall (not illustrated) first hose end section 200 or by the deformation of the outer wall. In yet another embodiment, the second end part 210 and the first end part 208, when combined, form the cavity 218. For example, a portion of a wall 232 of the first end part 208 and a portion of the outer wall 222 of the second end part 210 form the cavity 218.

Figure 3C:
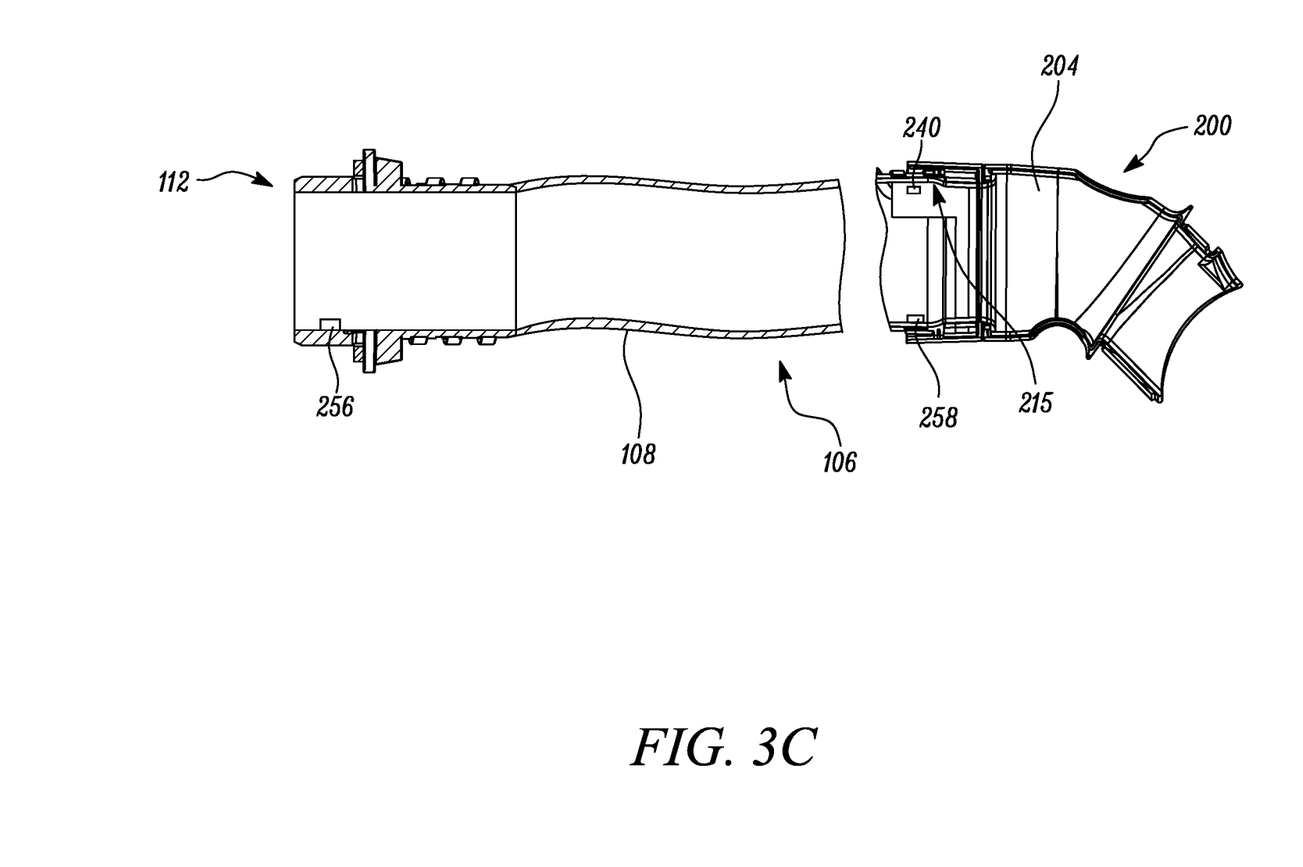
FIG. 3C illustrates a schematic view of the air hose associated with the warming system of FIG. 1, in accordance with one embodiment.
Figure 4:
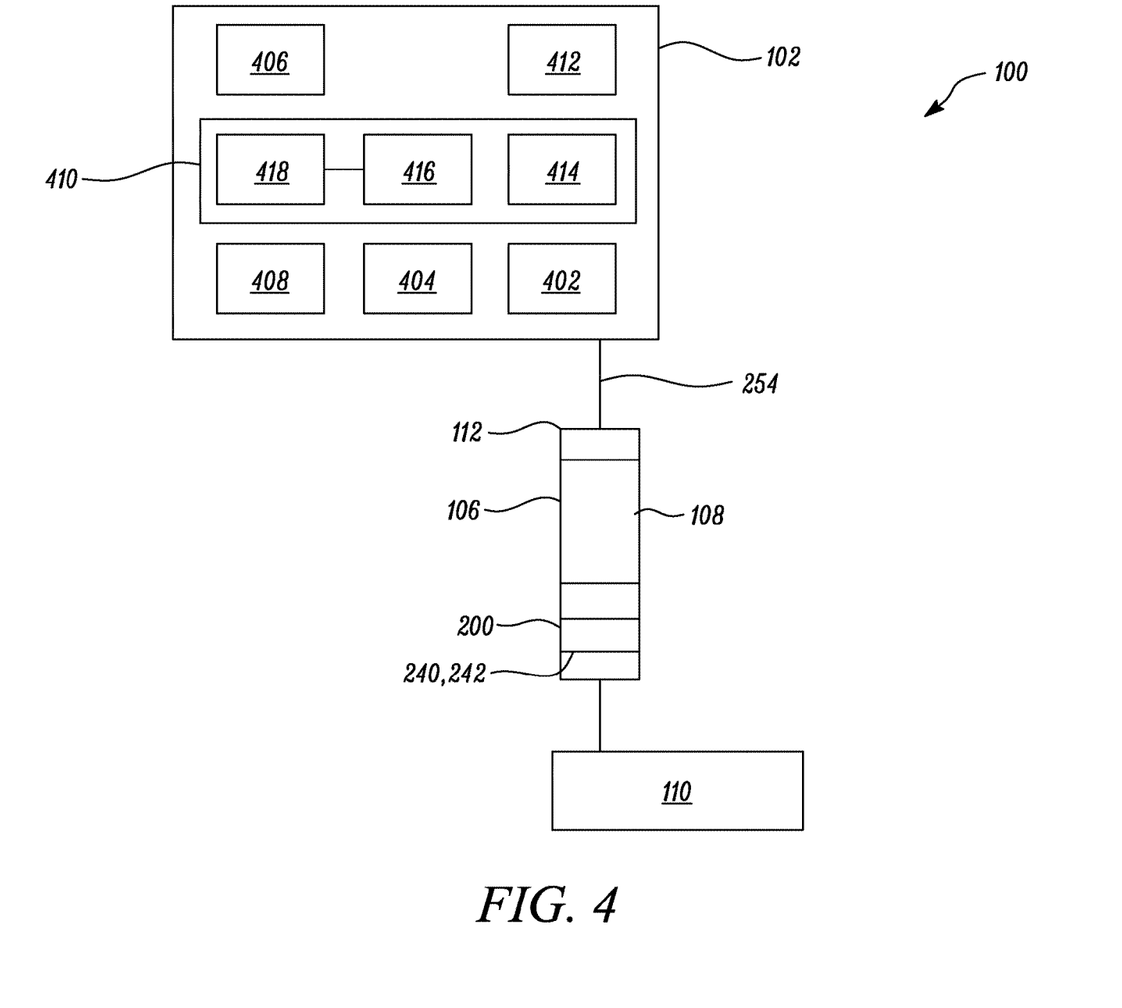
FIG. 4 illustrates a schematic representation of the warming system of FIG. 1, in accordance with one embodiment.

Further, the first hose end section 200 includes at least one pressure sensor 240 (and optionally a pressure sensor 242) communicatively coupled to the warming unit 102 (see FIGS. 1 and 4). It should be noted that the warming system 100 may operate with a single pressure sensor or multiple pressure sensors, as per application requirements. In an example, the pressure sensor 240 includes one pressure sensor 240. In some examples, the pressure sensor 240 can be disposed within the static pressure region 215. In one specific example, as illustrated in FIG. 3C, the pressure sensor 240 can be disposed proximate the inside surface 204 of the first hose end section 200.

In another example, as illustrated in FIG. 3A, the pressure sensor 240 can be positioned within the cavity 218. The pressure sensor 240 is isolated from the airflow path 206. Positioning of the pressure sensor 240 in the static pressure region 215, or the cavity 218, allows the pressure sensor 240 to gain a stable static pressure measurement. In other examples, the pressure sensor 240, 242 includes at least two pressure sensors 240, 242. In the illustrated example, the first hose end section 200 includes two pressure sensors 240, 242. In some examples, the first hose end section 200 may include a third pressure sensor 250 positioned on the circuit board 244. In such an example, the third pressure sensor 250 in the airflow path 206 can be used to measure dynamic pressure, which can be used to calculate a velocity of the pressurized, heated air. Further, in a situation where the warming system 100 includes a single pressure sensor, the pressure sensor can be subjected to testing so that the single pressure sensor can achieve appropriate pressure rise when the warming system 100 is turned on. Further, a failure rate of one of the pressure sensors 240, 242, 250 is typically less than failure due to port blockage, excessive temperature effects of an environment of the cavity 218, etc.

In some examples, the first hose end section 200 may include a flow rate sensor (not shown) that may be positioned proximate the inside surface 204 of the first hose end section 200. Further, the flow rate sensor may be in fluid communication with the airflow path 206. In one example, the flow rate sensor may detect a flow rate of the airflow 254 based on thermal mass flow measurement. The flow rate sensor 247 may embody a thermal mass flow sensor, or any other type of sensor, without any limitations.

Moreover, the first hose end section 200 includes the circuit board 244 including the pressure sensor 240, 242, 250, wherein a part 245 of the circuit board 244 is disposed outside of the cavity 218. The part 245 of the circuit board 244 is disposed transversely across a second opening 246 of the first hose end section 200. More particularly, a part 248 of the circuit board 244 is disposed within the cavity 218, whereas the part 245 of the circuit board 244 is disposed outside of the cavity 218. The circuit board 244 is L-shaped. In some examples, the circuit board 244 can include at least three pressure sensors 242, 244, 250. The pressure sensors 240, 242, 250 are positioned on the circuit board 244. Moreover, the air hose 106 includes a wire 252 disposed longitudinally in the corrugated flexible hose 108. The circuit board 244 or the pressure sensor 240, 242, 250 is electrically coupled to the wire 252.

The air hose 106 further includes a second hose end section 112 (shown in FIG. 1) mechanically coupled to the corrugated flexible hose 108 (see FIG. 1). The second hose end section 112 is configured to couple to the warming unit 102. More particularly, the second hose end section 112 allows coupling of the air hose 106 (see FIG. 1) with the warming unit 102 (see FIG. 1). In some examples, the second hose end section 112 can be coupled to the warming unit 102 using helical threads or the second hose end section 112 can be press fitted to the warming unit 102. Further, any other coupling technique may be used to couple the second hose end section 112 to the warming unit 102. The second hose end section 112 can be elbow shaped. The second hose end section 112 can be made of a plastic material.

Referring to FIG. 3C, the air hose 106 includes an inlet temperature sensor 256 and an outlet temperature sensor 258. The inlet temperature sensor 256 can be mounted proximate an entry side of the air hose 106. In one example, the second hose end section 112 can include the inlet temperature sensor 256. In another example, the corrugated flexible hose 108 can include the inlet temperature sensor 256. Moreover, the outlet temperature sensor 258 may be mounted proximate an exit end of the air hose 106. In one example, as illustrated herein, the first hose end section 200 can include the outlet temperature sensor 258. In another example, the corrugated flexible hose 108 can include the outlet temperature sensor 258. The inlet temperature sensor 256 and the outlet temperature sensor 258 may be used to determine a temperature difference across the air hose 106. It should be noted that a position of the inlet temperature sensor 256 and an outlet temperature sensor 258 illustrated herein is exemplary in nature.

Figure 3D:
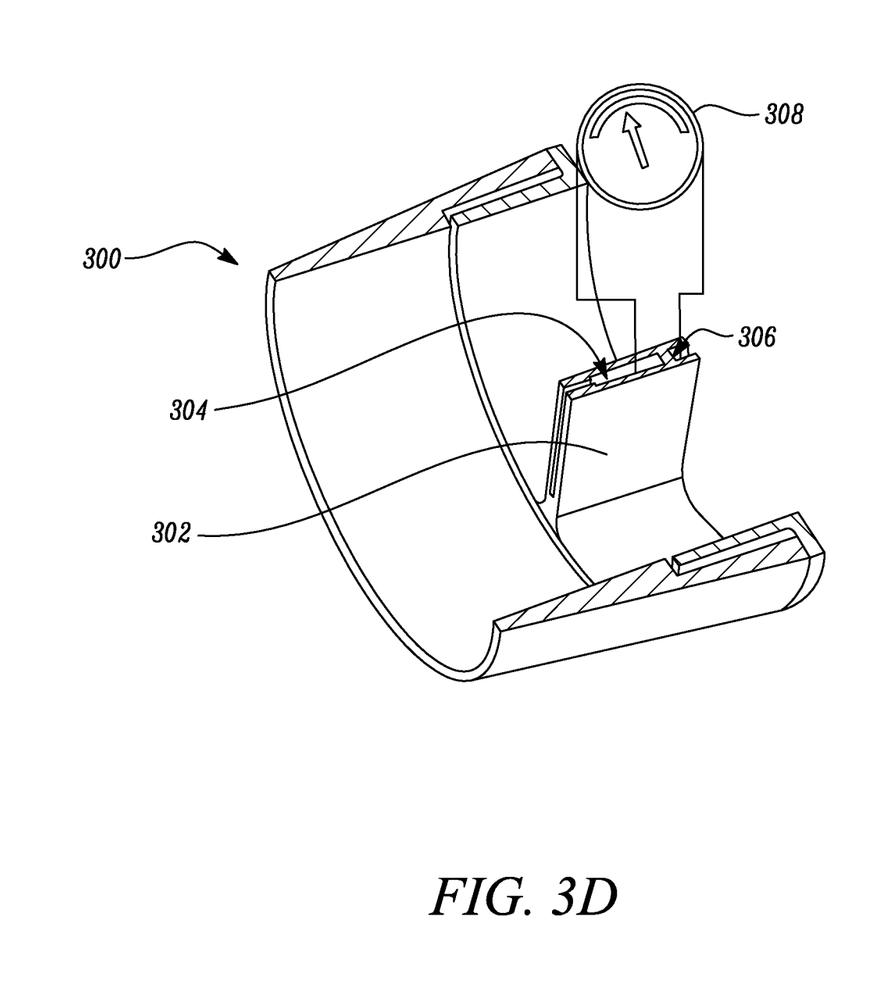
FIG. 3D illustrates a portion of a first hose end section associated with the warming system of FIG. 1 having a first sensor, in accordance with one embodiment.
Figure 3E:
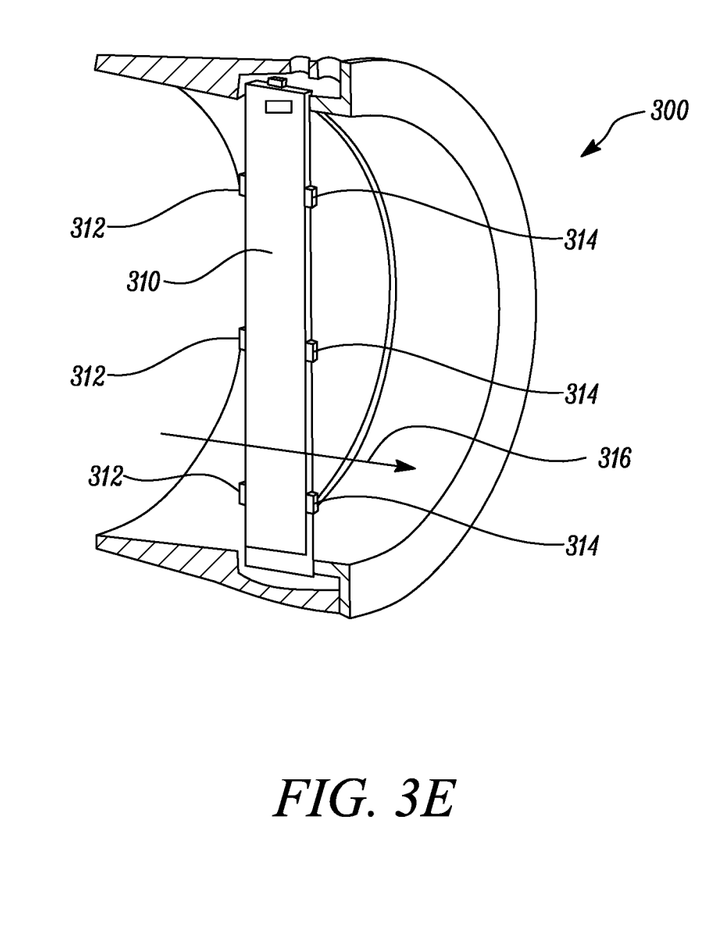
FIG. 3E illustrates the first hose end section of FIG. 3D having a number of second sensors and a number of third sensors, in accordance with another embodiment.

FIGS. 3D and 3E illustrate different techniques for determining a flow rate reading of the airflow 254 (see FIG. 4). Referring to FIG. 3D, an exemplary first hose end section 300 is illustrated. The first hose end section 300 may include a strut 302 defining a first air channel 304 and a second air channel 306. The first and second air channels 304, 306 are in communication with a first sensor 308. The first sensor 308 may be communicably coupled to the warming unit 102 (see FIG. 1). The first sensor 308 may be embodied as a differential pressure transducer herein that may be used to determine the flow rate reading of the airflow 254 (see FIG. 4).

Referring now to FIG. 3E, the first hose end section 300 may include a circuit board 310. Further, a number of second sensors 312 and a number of third sensors 314 may be positioned on the circuit board 310. The second and third sensors 312, 314 may be deployed at a center of an airflow path 316. In this example, the second and third sensors 312, 314 may be embodied as pressure sensors, temperature sensors, air flow sensors, or combinations thereof. The second sensors 312 may detect an impact pressure of the airflow 254 (see FIG. 4) and the third sensors 314 may detect a downstream pressure of the airflow 254 relative to the circuit board 310. Further, the impact pressure and the downstream pressure may be used to derive the flow rate reading of the airflow 254 using Bernoulli's principle.

FIG. 4 illustrates the warming system 100 including the warming unit 102. The warming unit 104 can include a plug (not shown). The plug allows connection of electrical and electronic components of the warming unit 102 to a main power source (not shown). The warming unit 102 includes a heater 402 and an air mover 404. The heater 402 and the air mover 404 are positioned within a housing 114 (shown in FIG. 1) of the warming unit 102. The heater 402 and the air mover 404 generate and provide the stream of pressurized, heated air. When the heater 402 and the air mover 404 are operated, the stream of pressurized, heated air is directed to the pneumatic convective device 110 via the air hose 106. Further, a filter (not shown) can be positioned at an inlet side of the air mover 404 that removes dust or dirt from ambient air before the ambient air enters the air mover 404. The filter may be integral with the air mover 404.

The air mover 404 varies a flow rate of the ambient air as per application requirements. The air mover 404 can be adapted to increase the pressure of the ambient air received by the air mover 404. The air mover 404 can include a commercially available blower unit, having a motor and an impeller or a compressor unit, that pressurizes air flowing therethrough. In some examples, the warming unit 102 can include an input device that allows a user to change settings of the air mover 404 in order to vary the pressure of air exiting the air mover 404 as desired. The input device can include a knob or a button. Further, the heater 402 is positioned downstream of the air mover 404. The heater 402 is adapted to increase a temperature of the air exiting the air mover 404. The heater 402 may embody a commercially available heating device that can have coil windings for transferring heat to the pressurized air flowing therethrough. In some examples, the warming unit 102 can include an input device associated with the heater 402 that allows the user to change settings of the heater 402 in order to vary the temperature of the air exiting the heater 402. The input device may include a knob or a button.

Further, the warming unit 102 includes an alert circuitry 406 that is configured to notify the user of a condition. Various conditions for which alerts or notifications can be provided will be explained later in this section. Moreover, the notifications can include a visual alert or an audible alert. For example, the notification in the form of the visual alert can be provided through a display screen (not shown). The visual alert can include text messages or graphical representation corresponding to various conditions. It should be noted that the display screen can be provided on the warming unit 102. Alternatively, the display screen can be provided remote to the warming unit 102. For example, the notifications can be provided to the user via a display screen of a hand-held device present with the user, without limiting the scope of the present disclosure. In some examples, the alerts or notifications can be provided based on flashing of lights. The lights can have different color coding corresponding to different conditions. In another example, the alerts or notifications in the form of the audible alert can be provided through a speaker. The audible alert can include a message, a single beep, a series of beeps, or a buzzer.

Further, the warming unit 102 includes a power conversion apparatus 408. The warming unit 102 includes the power conversion apparatus 408 for converting Alternating Current (AC) power for use by a heater control circuitry 410. The power conversion apparatus 408 can provide driving power to the heater 402, the air mover 404, and the alert circuitry 406. The warming unit 102 also includes the heater control circuitry 410. The heater control circuitry 410 is in communication with the power conversion apparatus 408 to receive power therefrom. Further, the heater control circuitry 410 is communicably coupled with the heater 402, the air mover 404, and the alert circuitry 406. The heater control circuitry 410 can control an operation of the heater 402 and the air mover 404, such as switching of the heater 402 and the air mover 404 between an on state and an off state.

The heater control circuitry 410 controls the airflow 254 and the temperature of the pressurized, heated air by modifying settings of the heater 402 and the air mover 404. More particularly, the heater control circuitry 410 can provide control signals to the heater 402 and the air mover 404 to vary the airflow 254 and the temperature of the pressurized, heated air, as per application requirements. Moreover, the pressure sensor 240, 242, 250 is communicatively coupled to the heater control circuitry 410. Additionally, the inlet temperature sensor 256 (see FIG. 3C), the outlet temperature sensor 258 (see FIG. 3C), the first sensor 308 (see FIG. 3D), the second sensors 312 (see FIG. 3E), and the third sensors 314 (see FIG. 3E) may be communicatively coupled to the heater control circuitry 410. In some examples, the warming system 100 also includes a data store 412. The data store 412 can be communicably coupled with the heater control circuitry 410. The data store 412 may store information pertaining to a pneumatic convective device profile. The pneumatic convective device profile is an identity of a pneumatic convective device type.

Components and functions of the heater control circuitry 410 will now be explained in detail. The heater control circuitry 410 can include a temperature sensor 414 for measuring ambient temperature outside of the airflow 254. Further, the heater control circuitry 410 includes a processor 416 and a memory 418 communicatively coupled to the processor 416. The memory 418 can store various processes, algorithms, and/or instructions therein. The memory 418 disclosed herein is configured to store various instructions which when executed by the processor 416 causes the heater control circuitry 410 to perform a variety of functions. In the illustrated example, the memory 418 stores a process 500 (shown in FIG. 5) which when executed by the processor 416 causes the heater control circuitry 410 to perform the variety of functions. The processor 416 can retrieve the process 500 from the memory 418 as and when necessary to execute functions pertaining to the warming system 100. The process 500 being executed by the processor 416 will now be explained in detail in relation to FIG. 5.

Figure 5:
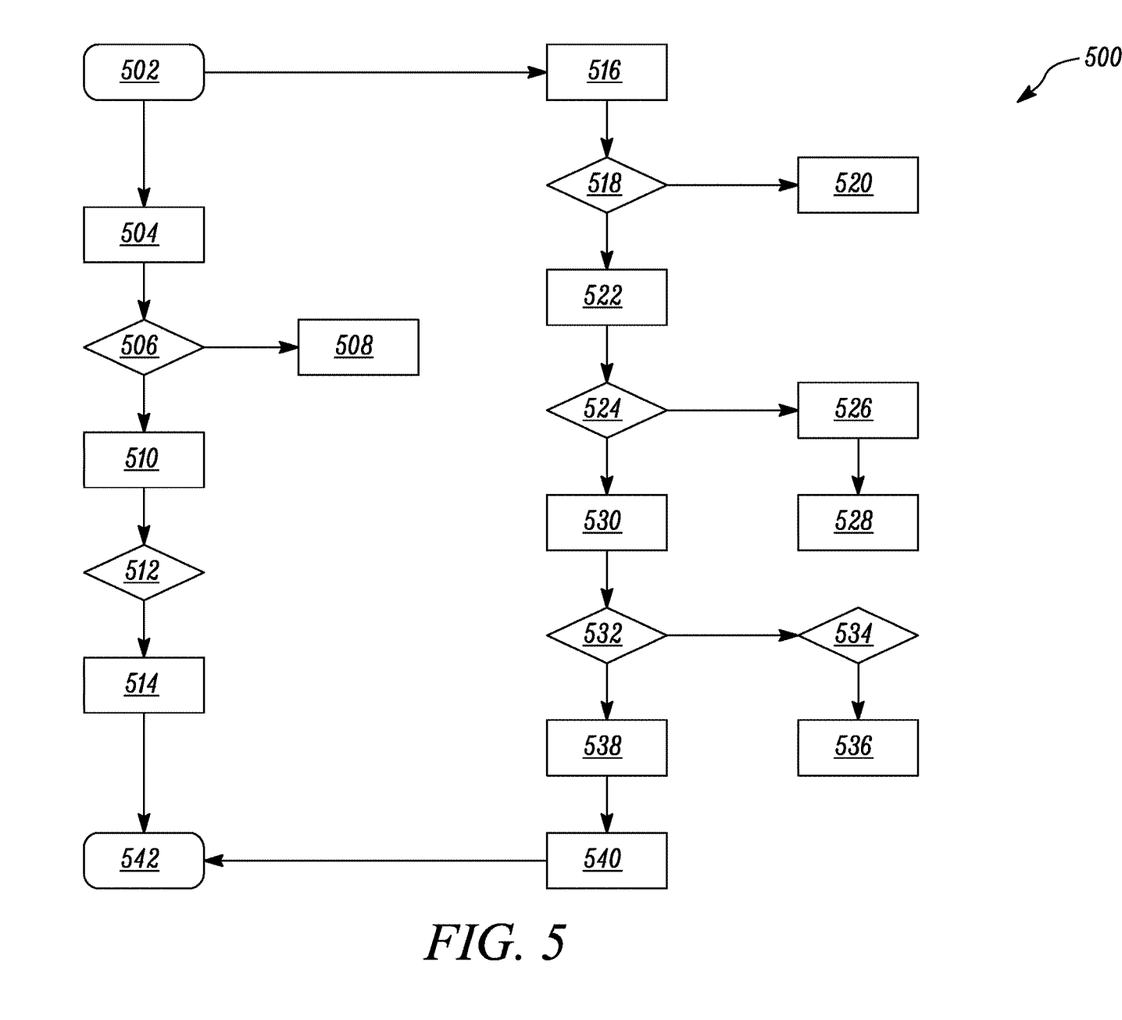
FIG. 5 illustrates a flowchart for a process of controlling one or more functions associated with the warming system of FIG. 1, in accordance with one embodiment.

FIG. 5 illustrates a flowchart for the process 500 of controlling one or more functions associated with the warming system 100. The process 500 begins or starts operation at a block 502. Further, the process 500 moves to a block 504 from the block 502. At the block 504, in one example, the processor 416 receives a first pressure reading from the pressure sensor 240, 242 and, optionally, the temperature difference across the air hose 106 based on readings from the inlet and outlet temperature sensors 256, 258. More particularly, the memory 418 includes instructions that, when processed by the processor 416, causes the processor 416 to receive the first pressure reading from the pressure sensor 240, 242 and the temperature difference across the air hose 106.

In some examples, the processor 416 may also receive a value of the ambient temperature from the temperature sensor 414. In other examples, the processor 416 may also receive a value of a rotation speed of the air mover 404. In the illustrated example, the first pressure reading can be an average of the pressure readings from each of the pressure sensors 240, 242. Alternatively, the first pressure reading can be received from one of the pressure sensors 240, 242. It should be noted that the first pressure reading may be received from one of the pressure sensors 240, 242 when the air mover 404 is operating in a steady state condition. Further, the process 500 moves to a block 506. At the block 506, the instructions also cause the processor 416 to determine whether the first pressure reading is within a first threshold. In some examples, the first pressure reading, the temperature difference across the air hose 106, and the ambient temperature may be used to determine whether the first pressure reading is within the first threshold. In other examples, the processor 416 may utilize the first pressure reading and the rotation speed of the air mover 404 to determine whether the first pressure reading is within the first threshold.

Accordingly, the processor 416 compares the first pressure reading with the first threshold. The first threshold is measured above a normal off pressure profile. The term "normal off pressure profile" can be indicative of a pressure in the air hose 106 during start-up of the warming system 100 or when the warming system 100 is in an off state. In some examples, the first threshold is no greater than 0.1 inches of water. Further, in an example, the first threshold is indicative of an absence of the pneumatic convective device 110. More particularly, the absence of the pneumatic convective device 110 may correspond to a condition of free hosing. In another example, the first threshold is indicative of an improperly installed pneumatic convective device 110 characterized by a lack of an airtight seal between the pneumatic convective device 110 and the air hose 106. More particularly, the first threshold is indicative of a leakage at a junction of the pneumatic convective device 110 and the air hose 106.

Further, the instructions cause the processor 416 to perform at least one action based on the first pressure reading being within the first threshold. More particularly, the process 500 moves to a block 508 if the first pressure reading is within the first threshold. At the block 508, the instructions cause the processor 416 to perform the at least one action. In one example, the at least one action includes activating the alert circuitry 406. More particularly, the alert circuitry 406 can be activated to notify the user regarding the absence of the pneumatic convective device 110 or the improperly installed pneumatic convective device 110. In another example, the at least one action includes deactivating the heater 402 or the air mover 404. More particularly, if the processor 416 detects that the first pressure reading is within the first threshold, the processor 416 can issue control signals to the heater control circuitry 410 to switch the heater 402 or the air mover 404 to the off state. Such an action can be performed as a preventive measure to eliminate a possibility of thermal injuries to the patient in case of free hosing.

Further, in another example, at the block 504, the processor 416 receives the first pressure reading from the pressure sensor 240, 242 and the flow rate reading of the airflow 254. More particularly, the memory 418 includes instructions that, when processed by the processor 416, causes the processor 416 to receive the first pressure reading from the pressure sensor 240, 242 and the flow rate reading. The flow rate reading may be calculated using the techniques explained in FIGS. 3D and 3E. Further, the process 500 moves to a block 506. At the block 506, the instructions also cause the processor 416 to determine whether a ratio of the flow rate reading to the first pressure reading is within a predetermined threshold. The term "predetermined threshold" as referred to herein may be indicative of a threshold ratio of pressure to flow rate below which the condition of free hosing may be observed.

Accordingly, the processor 416 compares the ratio of the flow rate reading to the first pressure reading with the predetermined threshold. Further, in an example, the predetermined threshold is indicative of the absence of the pneumatic convective device 110. More particularly, the absence of the pneumatic convective device 110 may correspond to the condition of free hosing. In another example, the predetermined threshold is indicative of the improperly installed pneumatic convective device 110 characterized by the lack of the airtight seal between the pneumatic convective device 110 and the air hose 106. More particularly, the predetermined threshold is indicative of the leakage at the junction of the pneumatic convective device 110 and the air hose 106.

Further, the instructions cause the processor 416 to perform the at least one action based on the ratio of the flow rate reading to the first pressure reading being within the predetermined threshold. More particularly, the process 500 moves to the block 508 if the ratio of the flow rate reading to the first pressure reading is within the first threshold. At the block 508, the instructions cause the processor 416 to perform the at least one action. In one example, the at least one action includes activating the alert circuitry 406. More particularly, the alert circuitry 406 can be activated to notify the user regarding the absence of the pneumatic convective device 110 or the improperly installed pneumatic convective device 110. In another example, the at least one action includes deactivating the heater 402 or the air mover 404. More particularly, if the processor 416 detects that the ratio of the flow rate reading to the first pressure reading is within the predetermined threshold, the processor 416 can issue control signals to the heater control circuitry 410 to switch the heater 402 or the air mover 404 to the off state. Such an action can be performed as a preventive measure to eliminate the possibility of thermal injuries to the patient in case of free hosing.

Further, if the first pressure reading is greater than the first threshold, the process 500 moves to a block 510. At the block 510, the processor 416 receives a second pressure reading from the pressure sensor 240, 242. More particularly, the memory 418 includes instructions that, when executed by the processor 416, cause the processor 416 to receive the second pressure reading from the pressure sensor 240, 242. In the illustrated example, the second pressure reading can be an average of the pressure readings from each of the pressure sensors 240, 242. Alternatively, the second pressure reading can be received from one of the pressure sensors 240, 242.

Further, the process 500 moves to a block 512. At the block 512, the instructions also cause the processor 416 to determine whether the second pressure reading is within a second threshold. Accordingly, the processor 416 compares the second pressure reading with the second threshold. The second threshold is at least 1.5 inches of water. Further, in an example, the second threshold can be indicative of a blockage that causes the second pressure reading to correspond with the second threshold. The blockage can be present at the first hose end section 200, the second hose end section 112, or at inlets/outlets of the heater 402 and/or the air mover 404. In other examples, the second pressure reading may correspond with the second threshold due to folding/furling of the pneumatic convective device 110, which may either cause blockage of the air hose 106 or inefficient distribution of the airflow 254 within the pneumatic convective device 110. In yet other examples, the blockage can be due a fold in the air hose 106 that restricts the airflow 254 therethrough. The blockage may also be present in the filter or at any location that is upstream of the pressure sensors 240, 242.

It should be noted that the processor 416 determines the presence of the blockage based on the temperature difference across the air hose 106. More particularly, the processor 416 may receive temperature readings from the inlet temperature sensor 256 and the outlet temperature sensor 258 to determine the temperature difference across the air hose 106. If the temperature difference is higher than a predetermined temperature threshold value, the processor 416 may determine and indicate the presence of the blockage.

In some examples, the second threshold can be indicative of the condition of free hosing that may cause the second pressure reading to correspond with the second threshold. It should be noted that the processor 416 determines the condition of free hosing based on the temperature difference across the air hose 106. More particularly, if the temperature difference is lower than the predetermined temperature threshold value or if the temperature difference is minimal, the processor 416 may determine and indicate the condition of free hosing.

Moreover, the instructions further cause the processor 416 to perform at least one action based on the second pressure reading being within the second threshold. More particularly, the process 500 moves to a block 514 if the second pressure reading is within the second threshold. At the block 514, the instructions cause the processor 416 to perform the at least one action. In one example, the at least one action includes activating the alert circuitry 406. More particularly, the alert circuitry 406 can be activated to notify the user regarding the blockage. In another example, the at least one action includes deactivating the heater 402 or the air mover 404. In yet another example, the at least one action includes reducing the airflow 254 or the temperature of the airflow 254. More particularly, if the processor 416 detects that the second pressure reading is within the second threshold, the processor 416 can issue control signals to the heater control circuitry 410 to either switch the heater 402 or the air mover 404 to the off state or reduce the airflow 254 or the temperature of the airflow 254. Such an action can be performed as a preventive measure to eliminate a possibility of insufficient therapy being provided to the patient by the warming system 100 and also prevent overheating of the warming system 100.

Further, the process 500 also performs a parallel set of operations and moves to a block 516 from the block 502. At the block 516, the processor 416 receives a third pressure reading from the pressure sensor 240, 242. More particularly, the memory 418 includes instructions that, when executed by the processor 416, cause the processor 416 to receive the third pressure reading from the pressure sensor 240, 242. In the illustrated example, the third pressure reading can be an average of the pressure readings from each of the pressure sensors 240, 242. Alternatively, the third pressure reading can be received from one of the pressure sensors 240, 242. Further, the process 500 moves to a block 518. At the block 518, the instructions cause the processor 416 to determine whether the third pressure reading corresponds to the pneumatic convective device profile. Accordingly, the processor 416 compares the third pressure reading with the pneumatic convective device profile.

Moreover, the instructions cause the processor 416 to perform at least one action in response to the pneumatic convective device profile. More particularly, the process 500 moves to a block 520 if the second pressure reading corresponds to the pneumatic convective device profile. At the block 520, the instructions cause the processor 416 to perform the at least one action. In an example, the at least one action includes communicating to the data store 412 that the pneumatic convective device profile is present. More particularly, the pneumatic convective device profile corresponding to the pneumatic convective device 110 that is being currently used with the warming system 100 can be communicated to the data store 412. Further, in another example, the at least one action includes adjusting the heater 402 and the air mover 404 to a predetermined setting for the pneumatic convective device profile. More particularly, the processor 416 may adjust the heater 402 or the air mover 404 to the predetermined settings that correspond to the type of the pneumatic convective device 110 connected with the air hose 106.

The process 500 further moves to a block 522 from the block 518. At the block 522, the processor 416 receives a series of pressure readings for the specific pneumatic convective device profile. More particularly, the memory 418 includes instructions that, when executed by the processor 416, cause the processor 416 to receive the series of pressure readings for the specific pneumatic convective device profile. The processor 416 receives the series of pressure readings from the pressure sensor 240, 242.

Further, the process 500 moves to a block 524. At the block 524, the processor 416 analyzes the series of pressure readings for the specific pneumatic convective device profile. In an example, at the block 524, the instructions also cause the processor 416 to determine whether the series of pressure readings indicates at least one of a blockage, a leak, and a missing filter. In one example, the series of pressure readings is increasing. More particularly, at the block 524, the processor 416 may determine that the series of pressure readings is increasing. In such an example, the increasing pressure readings within the series of pressure readings indicates the blockage. For example, the blockage may be present in the filter that may cause reduction in an amount of air being delivered to the air mover 404. It should be noted that the processor 416 determines presence of the blockage based on the series of pressure readings and the temperature difference across the air hose 106. More particularly, the processor 416 may receive temperature readings from the inlet temperature sensor 256 and the outlet temperature sensor 258 to determine the temperature difference across the air hose 106. If the temperature difference is higher than the predetermined temperature threshold value and the series of pressure readings is increasing, the processor 416 may determine the presence of the blockage.

Thus, based on the series of increasing pressure readings and the temperature difference across the air hose 106, the processor 416 may determine the blockage in the warming system 100. Further, if the series of pressure readings is increasing, the process 500 moves to a block 526. At the block 526, the instructions may cause the processor 416 to activate the alert circuitry 406 in response to the determination. In an example, the alert circuitry 406 may be activated to issue a notification indicative of a need of replacement of the filter. In another example, the alert circuitry 406 may be activated to issue a notification regarding a possibility of the blockage in the filter so that the filter may be cleaned.

In a second example, the series of pressure readings may indicate an instant drop or decrease in the pressure. In such an example, at the block 524, the processor 416 may determine a decrease in the series of pressure readings. In some examples, the decrease in the series of pressure readings indicates the leak in the system 100. In another example, the decrease in the series of pressure readings indicates the missing filter. In yet another example, the decrease in the series of pressure readings can indicate a condition of free hosing. Further, if the series of pressure readings is decreasing, the process 500 moves to a block 528. At the block 528, the instructions may cause the processor 416 to perform at least one action based on the decreasing pressure readings. In one example, the at least one action includes activating the alert circuitry 406. More particularly, the alert circuitry 406 can be activated to notify the user regarding a possibility of the leak in the system 100 or the missing filter. In other examples, the alert circuitry 406 can be activated to notify the user regarding the condition of free hosing.

According to an embodiment of the present disclosure, the memory 418 includes instructions that, when executed by the processor 416, cause the processor 416 to receive a pressure reading while the pneumatic convective device 110 is attached and the temperature difference across the air hose 106. More particularly, the process 500 moves to a block 530 from the block 524. At the block 530, the processor 416 receives the pressure reading while the pneumatic convective device 110 is attached. The processor 416 receives the pressure reading from the pressure sensor 240, 242. The processor 416 also receives the temperature difference across the air hose 106. In some examples, the processor 416 may also receive the value of the ambient temperature measured by the temperature sensor 414. In other examples, the processor 416 may receive the value of the rotation speed of the air mover 404.

Further, the process 500 moves to a block 532. At the block 532, the instructions cause the processor 416 to compare the pressure reading to the pneumatic convective device profile for the pneumatic convective device 110. More particularly, at the block 532, the processor 416 compares the detected pressure reading to an expected pressure reading for the pneumatic convective device profile. If the detected pressure reading is different from the expected pressure reading, the process 500 moves to a block 534. At the block 534, the instructions cause the processor 416 to determine a condition based on a difference between the pressure reading and the expected pressure reading for the pneumatic convective device profile. In an example, the difference is associated with the temperature of the airflow 254. In order to determine whether the difference is associated with the temperature of the airflow 254, the processor 416 receives a value of the temperature of the airflow 254 based on readings from the temperature sensors 256, 258 and the value of the ambient temperature outside of the airflow 254 from the temperature sensor 414. In examples where a difference between the temperature of the airflow 254 and the ambient temperature outside of the airflow 254 is greater than a threshold, the processor 416 may determine that the difference between the pressure reading and the expected pressure is associated with the temperature of the airflow 254. In another example, the difference is associated with the airflow 254. Further, in some examples, the condition is a tear in the pneumatic convective device 110, contact between the first end part 208 (see FIGS. 2 and 3) and a layer of the pneumatic convective device 110, or combinations thereof.

Further, once the processor 416 determines the condition due to which the detected pressure reading is different from the expected pressure reading, the process 500 moves to a block 536. At the block 536, the instructions cause the processor 416 to communicate the condition. It should be noted that the condition can be communicated to the user based on activation of the alert circuitry 406. More particularly, the alert circuitry 406 can be activated to notify the user regarding a possibility of the tear in the pneumatic convective device 110, contact between the first end part 208 and the layer of the pneumatic convective device 110, or both. In some examples, the processor 416 also communicates the condition to the heater control circuitry 410. The heater 402 or the air mover 404 may adjust characteristics of the temperature of the airflow 254 or the airflow 254 based on inputs received from the heater control circuitry 410. In one example, the air mover 404 adjusts the airflow 254 from a first airflow to a second airflow based on the difference. Accordingly, the difference between the pressure reading and the expected pressure reading for the pneumatic convective device profile may be reduced.

Further, if the detected pressure reading corresponds to the expected pressure reading, the process 500 moves to a block 538 from the block 532. At the block 538, the processor 416 predicts a rise time to fully inflate the pneumatic convective device 110 based on a series of pressure readings. More particularly, the processor 416 also includes instructions that, when executed by the processor 416, cause the processor 416 to predict the rise time to fully inflate the pneumatic convective device 110 based on the series of pressure readings. Moreover, the processor 416 may also consider the type of pneumatic convective device 110 for predicting the rise time. For this purpose, the processor 416 may communicate with the data store 412 to determine the pneumatic convective device profile corresponding to the pneumatic convective device 110 that is being currently used with the warming system 100. As mentioned earlier, the pneumatic convective device profile is communicated to the data store 412 at the block 520. Further, the process 500 moves to a block 540 at which the processor 416 may activate the alert circuitry 406. Thus, the predicted rise time can be communicated to the user by the alert circuitry 406.

Moreover, the process 500 moves to a block 542 after processing the instructions at the block 514, 540. At the block 542, the process 500 may terminate or end operation. In the illustrated example, the processor 416 moves to the block 504, 516 simultaneously to run the associated instructions in a parallel manner. However, it may be contemplated that the instructions at the block 516 may be initiated in a series manner after the process 500 reaches the block 514, without limiting the scope of the present disclosure. It should be noted that the process 500 may operate/run on a real time basis as and when the warming system 100 is activated and used so that a usability and effectiveness of the warming system 100 may be improved.

The warming system 100 described herein may provide improved usability by issuing alerts or altering the characteristics of the airflow 254 based on determinations made by the processor 416 of the heater control circuitry 410. More particularly, the warming unit 102 provides notifications or alters one or more operating settings of the warming unit 102 if the processor 416 detects that the warming system 100 is not being used as expected.

Figure 6:
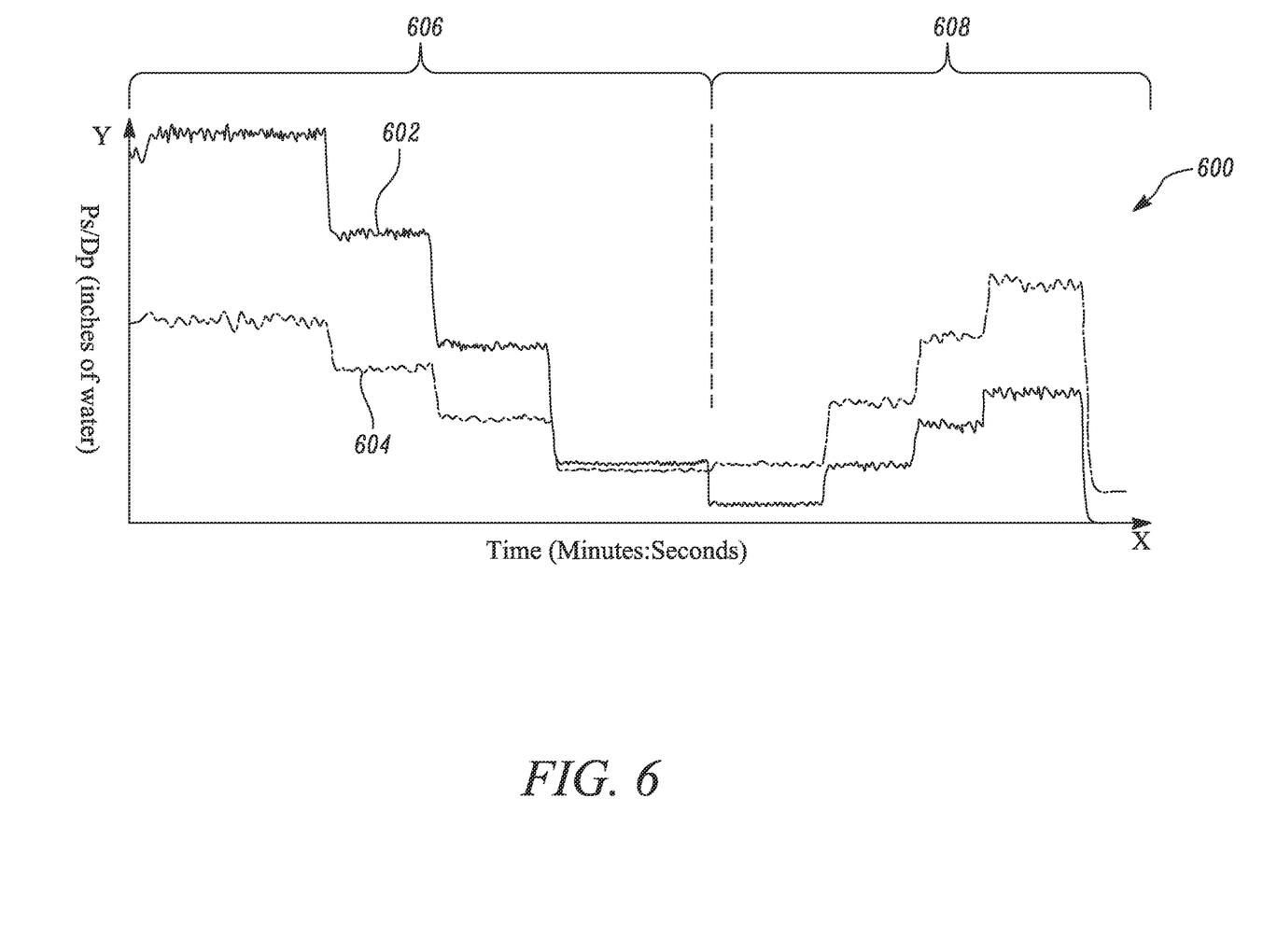
FIG. 6 illustrates an exemplary plot illustrating effects of flow rates on pressure measurements by pressure sensors disposed in the first hose end section, in accordance with one embodiment.

Referring now to FIG. 6, an exemplary plot 600 is illustrated. More particularly, the plot 600 illustrates effects of flow rates on pressure measurements in the first hose end section 200 (see FIG. 3A) when the pneumatic convective device 110 (see FIG. 1) is attached and during a condition of free hosing. A series of experiments were performed using the warming system 100 (see FIG. 1) to determine various values of total pressure "Dp" measurements (inches of water) and static pressure "Ps" measurements (inches of water) from which the flow rate (Standard Cubic Feet Per Minute) of the airflow 254 can be derived by using Bernoulli's equation. The flow rates can also be measured using a flow rate sensor, such as a thermal mass flow sensor. Further, the "Ps" measurements were performed using pressure sensors (similar to the pressure sensors 240, 242, 250 and positioned at locations similar to the locations of position of the pressure sensors 240, 242, 250). Moreover, the "Dp" measurements were performed using the flow rate measurement technique described in relation to FIG. 3D using the first sensor 308.

The plot 600 illustrates various values for time (in minutes: seconds) marked on X-axis and various values for the "Dp" measurements and the "Ps" measurements marked on Y-axis. Further, a first line 602 was plotted using various values of the "Ps" measurements determined during the experiment. Moreover, a second line 604 was plotted using various values of "Dp" determined during the experiment. In the plot 600, the readings of "Dp" and "Ps" in a first region 606 demonstrate readings with the pneumatic convective device 110, such as a blanket, and the readings of the "Dp" measurements and the "Ps" measurements in a second region 608 demonstrate readings conducted during the condition of free hosing. More particularly, comparatively lower values for the "Ps" measurements in the second region 608 as compared to the values for the "Ps" measurements in the first region 606 accounts for the condition of free hosing.

Further, the values of "Ps" are higher in the first region 606 and the values of "Dp" are lower than the values of "Ps" in the first region 606. Moreover, the values of "Dp" are higher in the second region 608 and the values of "Ps" are lower than the values of "Dp" in the second region 608. From the plot 600 and the associated experiment, it can be concluded that a ratio of "Dp"/"Ps" is higher in conditions of free hosing and lower when the pneumatic convective device 110 is connected to the warming system 100. Thus, the ratio of "Dp"/"Ps" can be used as an indication for detecting the condition of free hosing.

Although specific embodiments have been illustrated and described herein, it will be appreciated by those of ordinary skill in the art that a variety of alternate and/or equivalent implementations can be substituted for the specific embodiments shown and described without departing from the scope of the present disclosure. This application is intended to cover any adaptations or variations of the specific embodiments discussed herein. Therefore, it is intended that this disclosure be limited only by the claims and the equivalents thereof.

What is claimed is:

1. An air hose comprising:
a corrugated flexible hose;
a first hose end section mechanically coupled to the corrugated flexible hose, the first hose end section comprising a pressure sensor communicatively coupled to a warming unit, the first hose end section is configured to releasably couple to a pneumatic convective device,
wherein the first hose end section has an outside surface facing an environment and an inside surface facing an airflow path, the first hose end section comprises a static pressure region adjacent to the inside surface, the pressure sensor being disposed within the static pressure region wherein the static pressure region comprises a cavity,
wherein the first hose end section comprises a first end part and a second end part, the first end part is configured to releasably attach to the pneumatic convective device, the second end part is configured to attach to the corrugated flexible hose at one end such that a pneumatic seal is formed between the corrugated flexible hose and the second end part;
and wherein the second end part comprises the cavity, wherein the second end part comprises an inner wall and an outer wall, wherein a space between the inner wall and the outer wall forms the cavity; and
a second hose end section mechanically coupled to the corrugated flexible hose, the second hose end section is configured to couple to the warming unit.

2. The air hose of claim 1, further comprising an inlet temperature sensor and an outlet temperature sensor.

3. The air hose of claim 1, wherein the inside surface surrounds at least a portion of the airflow path.

4. The air hose of claim 1, wherein the first end part and the second end part are attached such that the first end part is rotatable about a longitudinal axis relative to the second end part.

5. The air hose of claim 1, wherein the static pressure region is a region of the first hose end section that isolates static pressure from the airflow path.

6. The air hose of claim 1, wherein an airflow path is longitudinal with the corrugated flexible hose and the first hose end section and the cavity is offset from the airflow path.

7. The air hose of claim 1, wherein the cavity is formed around at least half of an inner perimeter of the first hose end section.

8. The air hose of claim 1, wherein a distance between the inner wall and the outer wall is between 30 and 40 thousandths of an inch.

9. The air hose of claim 1, wherein the cavity forms an annulus that allows air from the airflow path to enter.

10. The air hose of claim 1, wherein the inner wall and the outer wall forms a first opening between an end of the inner wall and a recessed portion of the outer wall that allows air from the airflow path to enter.

11. The air hose of claim 1, wherein the first end part comprises a lip proximate an end of the first end part.

12. The air hose of claim 11, wherein the outer wall of the second end part comprises a recessed portion configured to mate with the lip such that the second end part is rotatable relative to the first end part.

13. The air hose of claim 1, wherein the second end part and the first end part, when combined, form the cavity.

14. The air hose of claim 13, wherein a portion of a wall of the first end part and a portion of an outer wall of the second end part form the cavity.

15. A system, comprising:
the air hose of claim 1;
a warming unit that can provide a stream of pressurized, heated air, comprising:
a heater control circuitry; and
a power conversion apparatus for converting Alternating Current (AC) power for use by the heater control circuitry.

* * * * *